United States Patent
Sesi

(10) Patent No.: US 9,610,199 B2
(45) Date of Patent: Apr. 4, 2017

(54) COMPRESSION STOCKING

(76) Inventor: Nasrin Sesi, Southfield, MI (US)

( * ) Notice: Subject to any disclaimer, the term of this patent is extended or adjusted under 35 U.S.C. 154(b) by 869 days.

(21) Appl. No.: 12/980,575

(22) Filed: Dec. 29, 2010

(65) Prior Publication Data

US 2012/0172922 A1 Jul. 5, 2012

(51) Int. Cl.
*A61B 17/00* (2006.01)
*A61F 13/08* (2006.01)

(52) U.S. Cl.
CPC .................................. *A61F 13/085* (2013.01)

(58) Field of Classification Search
CPC ...................................................... A61F 13/085
USPC ........................................... 606/201; 602/42
See application file for complete search history.

(56) References Cited

U.S. PATENT DOCUMENTS

| | | | |
|---|---|---|---|
| 2,513,639 A * | 7/1950 | Goodman | 2/239 |
| 3,538,914 A * | 11/1970 | Myers | 24/306 |
| 3,728,875 A * | 4/1973 | Hartigan et al. | 66/172 E |
| 4,166,463 A * | 9/1979 | Bloom | 602/63 |
| 5,450,630 A * | 9/1995 | Hale | 2/239 |
| 6,062,946 A | 5/2000 | Rosenberg | |
| 6,283,124 B1 | 9/2001 | Schleuning et al. | |
| 7,037,282 B2 | 5/2006 | Coleman | |
| 7,069,670 B1 * | 7/2006 | Gerke | 36/2 R |

FOREIGN PATENT DOCUMENTS

| | | |
|---|---|---|
| JP | 2002-115101 A | 4/2002 |
| KR | 10-2009-0061935 A | 6/2009 |

OTHER PUBLICATIONS

Aug. 28, 2012 International Search and Written Opinion.

* cited by examiner

*Primary Examiner* — Richard Louis
(74) *Attorney, Agent, or Firm* — Howard & Howard Attorneys PLLC

(57) ABSTRACT

A stocking for a compression-therapy patient comprises a foot portion matingly removably receiving and surrounding a foot. A closable/openable leg portion extends from the foot portion, removably receives a leg, defines adjoining edges of the leg portion, and includes a band defining an uppermost area of the leg portion and material of which is more compressive/supportive than a remainder thereof. A fastening device extends along the leg portion and continuously fastens/unfastens the edges to/from each other and closes/opens the leg portion such that the stocking can secure and apply continuous pressure to the foot/leg. The device includes a zipper and an enfoldment connected and secured along a continuous inner edge of the zipper, including material that is different than the band and/or remainder of the leg portion, and disposed between the zipper and skin and contacting the skin such that the enfoldment prevents the zipper from contacting the skin.

7 Claims, 1 Drawing Sheet

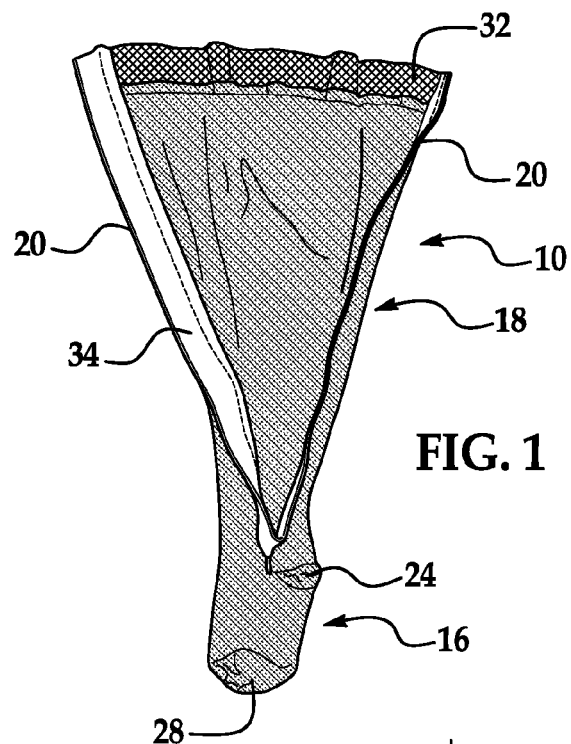
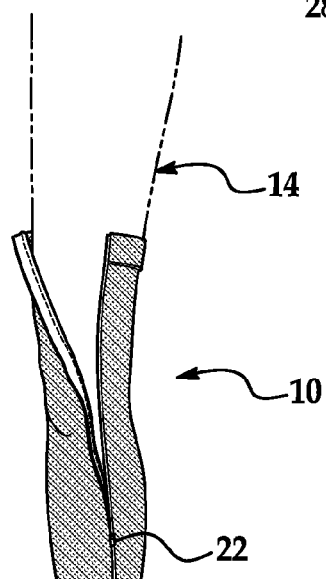
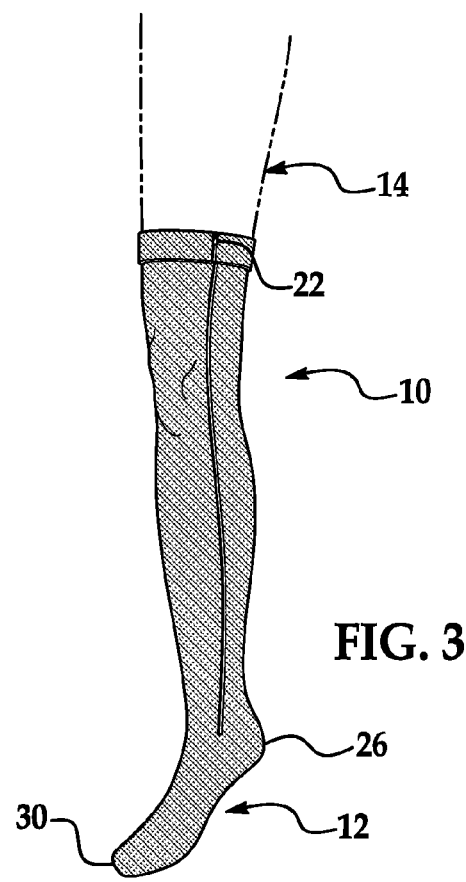
FIG. 1
FIG. 2
FIG. 3

COMPRESSION STOCKING

BACKGROUND OF THE INVENTION

1. Field of the Invention

The invention relates, generally, to compression garments and, more particularly, to a compression stocking.

2. Description of the Related Art

A compression stocking—such as a foot and leg stocking—is a medical garment designed specifically for applying continuous pressure to a foot and leg. The compression stocking known in the related art is typically made from an elastic material that can resiliently stretch around the foot and leg to provide compression therapy thereto. The stocking is commonly used in treating a variety of vascular- and circulatory-related conditions—such as lymphedema, chronic vein insufficiency (CVI), post-sclerotherapy, deep vein thrombosis, edema, varicose veins, spider veins, and other vein diseases and disorders. The stocking can also reduce other conditions of a leg and/or foot—including, but not limited to, those related to aching, burning, heaviness, numbing, poor circulation, swelling, tingling, and tiredness in or of the foot and/or leg—and inhibit progression of various venous disorders thereof.

Because the known compression stocking is necessarily tight-fitting, one common problem is difficulty in donning and doffing it. This problem is further exacerbated by the fact that many patients who wear the compression stocking are overweight, elderly, and/or suffer from arthritis. Such conditions can prevent these patients from possessing the amount of dexterity and strength commonly required for such donning and doffing. For example, the donning of the compression stocking requires the patient to slide the stocking over the free end of his or her foot and pull the stocking up and over the corresponding leg. Many patients either are unable to reach the foot or have insufficient strength to hold onto and pull the tight-fitting stocking over the foot and up along the leg. Of course, since the doffing of the compression stocking is essentially the reverse process of this, these patients also either have insufficient strength to hold onto and push the tight-fitting stocking down along the leg and off the foot or are unable to reach the foot.

Thus, there is a need in the related art for a compression stocking donning and doffing of which is relatively easy. More specifically, there is a need in the related art for a compression stocking donning and doffing of which requires a relatively less amount of dexterity and strength. There is a need in the related art for such a compression stocking donning and doffing of which also does not require the patient to hold onto the stocking and either pull it up or push it down along the corresponding leg.

SUMMARY OF INVENTION

The invention overcomes the disadvantages in the related art in a compression stocking for a compression-therapy patient. The compression stocking comprises a foot portion that is adapted to matingly removably receive and surround an entirety of a foot the patient. A closable and openable leg portion extends upwardly from a top of the foot portion, is adapted to removably receive at least a portion of a corresponding leg of the patient, defines adjoining edges of the leg portion, and includes a band that defines an uppermost area of the leg portion and material of which is more compressive and supportive with respect to material of which a remainder of the leg portion is made. A fastening device extends a substantial length of the leg portion arid is adapted to continuously fasten the adjoining edges to and unfasten the adjoining edges from each other and close and open the leg portion such that the compression stocking can secure and apply continuous pressure to the foot and leg. The fastening device includes a zipper and an enfoldment. The enfoldment is connected and secured along a continuous inner edge of the zipper, includes material that is different with respect to the material of which the band and/or remainder of the leg portion is made, and is disposed between the zipper and skin of the patient and contacts the skin such that the enfoldment prevents the zipper from contacting the skin.

One advantage of the compression stocking of the invention is that donning and doffing of it is relatively easy.

Another advantage of the compression stocking of the invention is that donning and doffing of it requires a relatively less amount of dexterity and strength.

Another advantage of the compression stocking of the invention is that donning and doffing of it does not require the patient to hold onto the stocking and either pull it up or push it down along the corresponding leg.

Another advantage of the compression stocking of the invention is that it is made of a comfortable, compressive, expansive, and supportive material that compresses to various degrees.

Another advantage of the compression stocking of the invention is that the foot and leg can be inserted into, secured within, and removed from the stocking relatively comfortably, easily, quickly, and, thus, struggle-free.

Another advantage of the compression stocking of the invention is that it can be employed with either foot/leg or both feet/legs of a user of the stocking.

Other objects, features, and advantages of the compression stocking of the invention will be readily appreciated as it becomes more understood while reading the subsequent detailed description of embodiments of the compression stocking taken in conjunction with accompanying drawings thereof.

BRIEF DESCRIPTION OF EACH FIGURE OF DRAWING OF INVENTION

FIG. 1 is a perspective view of an embodiment of a compression stocking of the invention showing the fastening device completely unfastening the adjoining edges from each other and, in turn, completely opening the leg portion.

FIG. 2 is an environmental view of the embodiment of the compression stocking of the invention illustrated in FIG. 1 showing it being worn on a foot and corresponding leg and the fastening device partially fastening the adjoining edges to each other and, in turn, partially closing the leg portion.

FIG. 3 is an environmental view of the embodiment of the compression stocking of the invention illustrated in FIG. 1 showing it being worn on a foot and corresponding leg and the fastening device completely fastening the adjoining edges to each other and, in turn, completely closing the leg portion.

DETAILED DESCRIPTION OF EMBODIMENTS OF INVENTION

Referring now to the figures, where like numerals are used to designate like structure, a compression stocking of the invention is generally indicated at 10. The compression stocking 10 is described and shown being employed with a foot, generally indicated at 12, and corresponding leg, generally indicated at 14, of a user of the compression stocking 10. The user can be, for example, a "compression therapy" patient, in which case the compression stocking 10 is being used to treat any of a variety of vascular- and circulatory-related conditions (vein diseases and disorders), reduce other conditions of the foot 12 and/or leg 14, or inhibit progression of various venous disorders of the foot 12 and/or leg 14.

However, it should be appreciated by those having ordinary skill in the related art that the compression stocking 10 can be employed with any other suitable part of the body of the user where compression therapy is desired, such as an arm and/or hand. It should also be appreciated that compression therapy is not limited to the treatment of the conditions, diseases, and disorders delineated above. It should also be appreciated that the compression stocking 10 is not limited to use in compression therapy, but can be used generally to apply continuous pressure to a given body part.

Referring back to the figures, the compression stocking 10 includes, in general, a foot portion, generally indicated at 16, that is adapted to matingly removably receive at least a portion of the foot 12. A closable and openable leg portion, generally indicated at 18, extends upwardly from a top of the foot portion 16, is adapted to removably receive at least a portion of the leg 14, and defines adjoining edges 20 of the leg portion 18. A fastening device, generally indicated at 22, extends a length of the leg portion 18 and is adapted to fasten the adjoining edges 20 to and unfasten the adjoining edges 20 from each other and, in turn, close and open the leg portion 18. In this way, the compression stocking 10 can secure and apply continuous pressure to the foot 12 and leg 14.

In one embodiment of the compression stocking 10 and as shown in the figures, the foot portion 16 is adapted to matingly receive an entirety of the foot 12. The foot portion 16 also defines a heel portion 24 designed to nestingly receive a corresponding heel 26 and a toe portion 28 designed to receive a corresponding set of toes 30. The material from which the heel portion 24 and toe portion 28 are made can be the same with respect to each other and different with respect to that of which the remainder of the foot portion 16 is made. More specifically, the material from which the interior and/or exterior of the heel portion 24 and toe portion 28 are made can be, for instance, more compressive, cushioned (padded), expansive, and/or supportive.

It should be appreciated by those having ordinary skill in the related art that the foot portion 16 can matingly receive any amount of the foot 12. It should also be appreciated that the foot portion 16 can be eliminated from the compression stocking 10. It should also be appreciated that the heel portion 24 and/or toe portion 28 can be eliminated from the foot portion 16. It should also be appreciated that the foot portion 16 can be made of a uniform material.

The leg portion 18 extends unitarily from the top of the foot portion 16 and is adapted to receive a substantial length of the leg 14. More specifically, the leg portion 18 can be designed to extend the entire length of the leg 14. The leg portion 18 also includes a band 32 that defines an uppermost area of the leg portion 18. The material from which band 32 is made can be different with respect to that of which the remainder of the leg portion 18 is made. More specifically, the material from which the interior and/or exterior of band 32 is made can be, for instance, more compressive, cushioned (padded), expansive, and/or supportive.

It should be appreciated by those having ordinary skill in the related art that the leg portion 18 can receive any length of the leg 14. It should also be appreciated that the leg portion 18 can be made of a uniform material.

The fastening device 22 extends substantially linearly an entirety of the length of the leg portion 18. More specifically, the fastening device 22 extends substantially from a lowermost point of the leg portion 18 to an uppermost portion of band 32 in a substantially straight line. The fastening device 22 is also adapted to continuously (as opposed to discretely) fasten the adjoining edges 20 to and unfasten the adjoining edges 20 from each other and, in turn, continuously (as opposed to discretely) close and open the leg portion 18. FIG. 1 shows the adjoining edges 20 completely unfastened from each other such that the leg portion is completely open; FIG. 2 shows the adjoining edges 20 only partially unfastened from each other such that the leg portion is only partially open; and FIG. 3 shows the adjoining edges 20 completely fastened to each other such that the leg portion is completely closed. The leg portion 18 also includes an enfoldment 34 that defines a continuous interior outline of the fastening device 22. The material from which the enfoldment 34 is made can be different with respect to that of which the remainder of the leg portion 18 (including band 32) is made. More specifically, the material from which the interior and/or exterior of the enfoldment 34 is made can be, for instance, more compressive, cushioned (padded), expansive, and/or supportive.

In one embodiment of the compression stocking 10 and as best shown in FIGS. 2 and 3, the fastening device is a zipper 22. The two rows of tiny interlocking tabs of the zipper 22 define the corresponding adjoining edges 20 of the leg portion 18, and the adjoining edges 20 are joined to and separated from each other by sliding the sliding part of the zipper 22 up and down, respectively.

It should be appreciated by those having ordinary skill in the related art that the fastening device 22 can extend any suitable length of the leg portion 18 in any suitable manner. It should also be appreciated that the fastening device 22 can fasten the adjoining edges 20 to and unfasten the adjoining edges 20 from each other and, in turn, close and open the leg portion 18 in any suitable manner. It should be appreciated also that the fastening device 22 can be any suitable device for fastening the adjoining edges 20 to and unfastening the adjoining edges 20 from each other and, in turn, closing and opening the leg portion 18 such that the compression stocking 10 can secure and apply continuous pressure to the foot 12 and leg 14. Thus, the fastening device 22 can include corresponding, interlocking components having Velcro® or any similar hook-and-loop type of fastener or any other suitable fastener of the type generally known in the related art.

The compression stocking 10 is made of a compressive, expansive, and supportive material that compresses to various degrees, such as nylon or spandex. However, it should be appreciated by those having ordinary skill in the related art that the compressive stocking 10 can be made of any material suitable for resiliently stretching around the foot 12 and leg 14 to apply continuous pressure to the foot 12 and leg 14, in general, or provide compression therapy to the foot 12 and leg 14, in particular. It should also be appreciated that the foot portion 12 and leg portion 14 can be made of a different material with respect to each other.

In operation, to don the compression stocking 10, the user completely manually unzips the zipper 22 such that the adjoining edges 20 are completely unfastened from each other and, thus, the leg portion 18 is completely open. The user then slides his or her foot 12 into the foot portion 16 such that the foot portion 16 matingly receives an entirety of the foot 12 and the heel portion 24 nestingly receives the heel 26. The user then sets the leg 14 within the leg portion 18 such that the leg portion 18 receives a substantial length of the leg 14. The user then completely manually zips the zipper 22 such that the adjoining edges 20 are completely fastened to each other and, thus, the leg portion 18 is completely closed. In this way, the compression stocking 10 secures and applies continuous pressure to the foot 12 and leg 14. Of course, the user does not have to completely zip and unzip the zipper 22. Rather, the user can zip and unzip the zipper 22 only to the extent necessary for the foot portion 16 to matingly receive an entirety of the foot 12, the heel portion 24 to nestingly receive the heel 26, and the leg portion 18 to receive a substantial length of the leg 14. Doffing of the compression stocking 10 is essentially the reverse process of this.

Donning and doffing of the compression stocking 10 is relatively easy, requires a relatively less amount of dexterity and strength, and does not require the patient to hold onto the compression stocking 10 and either pull up or push down the compression stocking 10 along the leg 14. Also, the compression stocking 10 is made of a comfortable, compressive, expansive, and supportive material that compresses to various degrees. Furthermore, the foot 12 and leg 14 can be inserted into, secured within, and removed from the compression stocking 10 relatively comfortably, easily, quickly, and, thus, struggle-free. In addition, the compression stocking 10 can be employed with either foot 12/leg 14 or both feet 12/legs 14 of a user of the compression stocking 10.

The compression stocking 10 has been described above in an illustrative manner. It is to be understood that the terminology that has been used above is intended to be in the nature of words of description rather than of limitation. Many modifications and variations of the compression stocking 10 are possible in light of the above teachings. Therefore, within the scope of the appended claims, the compression stocking 10 may be practiced other than as specifically described above.

What is claimed is:

1. A compression stocking for a compression-therapy patient comprises:
    a foot portion that is adapted to matingly removably receive and surround an entirety of a foot of the patient;
    a closable and openable leg portion that extends upwardly from a top of said foot portion, is adapted to removably receive at least a portion of a corresponding leg of the patient, defines adjoining edges of said leg portion, and includes a band that defines an uppermost area of said leg portion and material of which is more compressive and supportive with respect to material of which a remainder of said leg portion is made; and
    a fastening device that extends a substantial length of said leg portion and is adapted to continuously fasten said adjoining edges to and unfasten said adjoining edges from each other and close and open said leg portion such that the compression stocking can secure and apply continuous pressure to the foot and leg, said fastening device including a zipper and an enfoldment, wherein said enfoldment is connected and secured along a continuous inner edge of said zipper, includes material that is different with respect to the material of which at least one of said band and the remainder of said leg portion is made, and is disposed between said zipper and skin of the patient and contacting the skin such that said enfoldment prevents said zipper from contacting the skin.

2. A compression stocking as set forth in claim 1, wherein said foot portion defines a heel portion designed to nestingly receive a corresponding heel.

3. A compression stocking as set forth in claim 1, wherein said foot portion defines a toe portion designed to receive a corresponding set of toes.

4. A compression stocking as set forth in claim 1, wherein said fastening device extends substantially linearly an entirety of said length of said leg portion.

5. A compression stocking as set forth in claim 1, wherein said compression stocking is made of a compressive, expansive, and supportive material that compresses to various degrees.

6. A compression stocking as set forth in claim 5, wherein said compression stocking is made of nylon.

7. A compression stocking as set forth in claim 5, wherein said compression stocking is made of spandex.

* * * * *